US010441438B1

(12) United States Patent
Rahman et al.

(10) Patent No.: US 10,441,438 B1
(45) Date of Patent: Oct. 15, 2019

(54) PREOPERATIVE FEMORAL IMPLANT SIZING

(71) Applicant: Smith & Nephew, Inc., Memphis, TN (US)

(72) Inventors: Mohammed Rahman, Brooklyn, NY (US); Yangqiu Hu, San Antonio, TX (US); Kyle Lonidier, Olive Branch, MS (US)

(73) Assignee: Smith & Nephew, Inc., Memphis, TN (US)

( * ) Notice: Subject to any disclaimer, the term of this patent is extended or adjusted under 35 U.S.C. 154(b) by 106 days.

(21) Appl. No.: 15/686,787

(22) Filed: Aug. 25, 2017

Related U.S. Application Data

(60) Provisional application No. 62/380,077, filed on Aug. 26, 2016.

(51) Int. Cl.
| | |
|---|---|
| A61F 2/46 | (2006.01) |
| A61B 34/00 | (2016.01) |
| G06T 7/00 | (2017.01) |
| G06T 7/70 | (2017.01) |
| A61B 34/10 | (2016.01) |
| A61F 2/38 | (2006.01) |

(52) U.S. Cl.
CPC ............ *A61F 2/4657* (2013.01); *A61B 34/00* (2016.02); *G06T 7/0012* (2013.01); *G06T 7/70* (2017.01); *A61B 2034/105* (2016.02); *A61B 2034/108* (2016.02); *A61F 2/3859* (2013.01); *A61F 2002/4658* (2013.01); *A61F 2002/4668* (2013.01); *G06T 2207/30008* (2013.01)

(58) Field of Classification Search
CPC .................. A61F 2/4657; A61F 2/3859; A61F 2002/4668; A61F 2002/4658; G06T 7/70; G06T 7/0012; G06T 2207/30008; A61B 34/00; A61B 2034/108; A61B 2034/105
See application file for complete search history.

(56) References Cited

U.S. PATENT DOCUMENTS

| | | | | |
|---|---|---|---|---|
| 6,024,746 | A * | 2/2000 | Katz ..................... | A61B 17/154 606/102 |
| 9,351,842 | B2 * | 5/2016 | Todd ...................... | A61F 2/3836 |
| 2005/0267353 | A1 * | 12/2005 | Marquart .............. | A61B 17/154 600/411 |

(Continued)

*Primary Examiner* — Qian Yang
(74) *Attorney, Agent, or Firm* — Pepper Hamilton LLP

(57) ABSTRACT

A method according to one embodiment includes locating distal lateral and medial condyles and posterior lateral and medial condyles a femoral bone model, and determining a posterior resection plane based on locations of the distal lateral and medial condyles, one or more dimensions of a prospective femoral implant, and one or more surgical preferences. The method may further include determining a first distance between the posterior medial condyle and the posterior resection plane and a second distance between the posterior lateral condyle and the posterior resection plane, determining a difference between a target value and an average of the first distance and the second distance, wherein the target value is associated with a thickness of the prospective femoral implant, and selecting a desired femoral implant size based on the difference between the target value and the average determined for each of a plurality of possible femoral implant sizes.

20 Claims, 12 Drawing Sheets

(56) References Cited

U.S. PATENT DOCUMENTS

| | | | | |
|---|---|---|---|---|
| 2007/0038223 | A1* | 2/2007 | Marquart | A61B 34/20 606/86 R |
| 2008/0269596 | A1* | 10/2008 | Revie | G06F 19/00 600/424 |
| 2011/0295378 | A1* | 12/2011 | Bojarski | A61F 2/30942 623/20.35 |

* cited by examiner

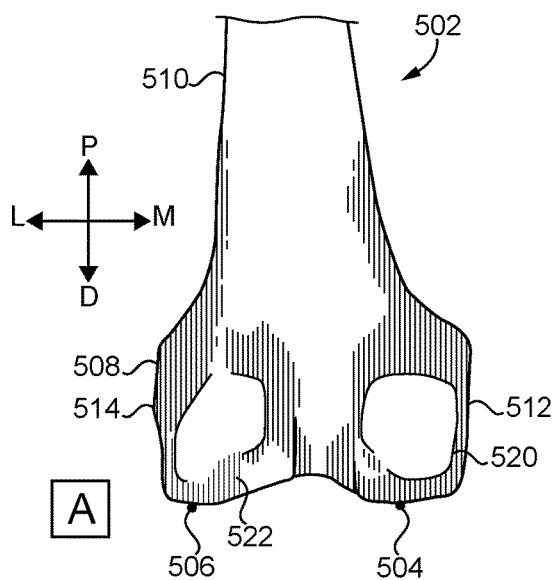
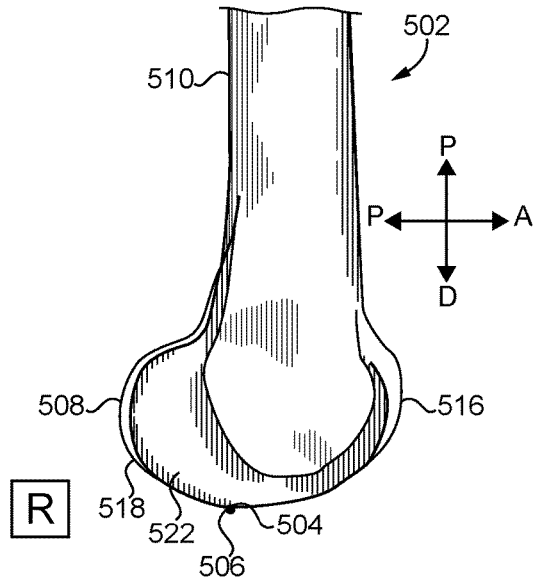
FIG. 5A  FIG. 5B
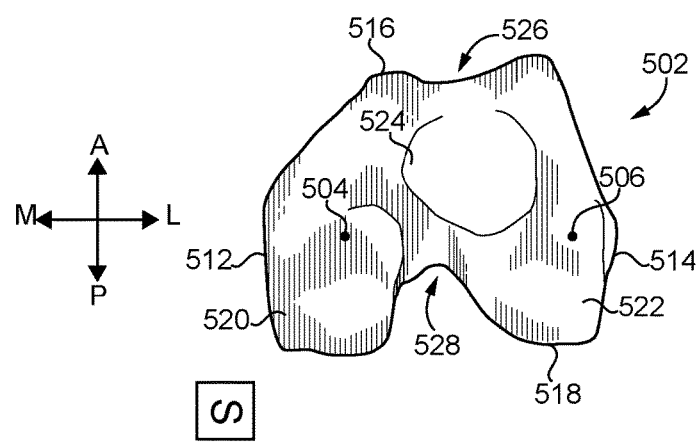
FIG. 5C

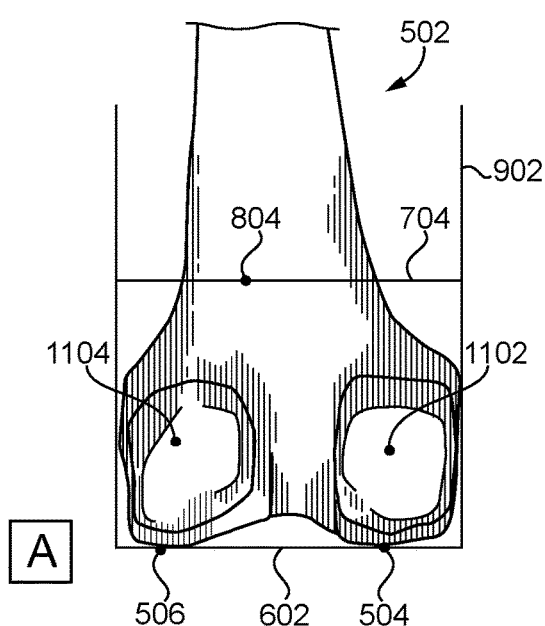
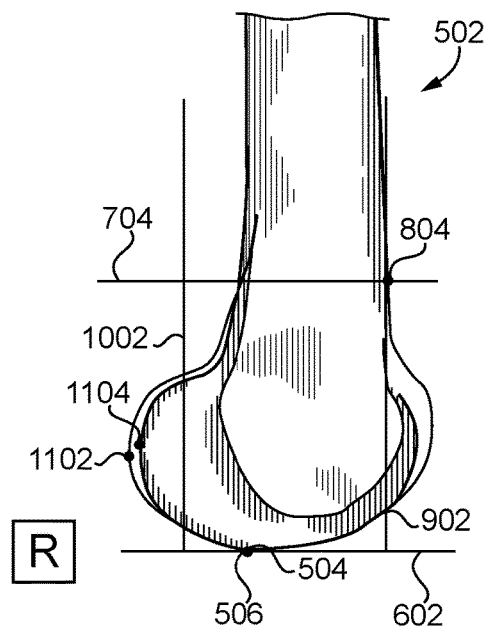
FIG. 11A    FIG. 11B
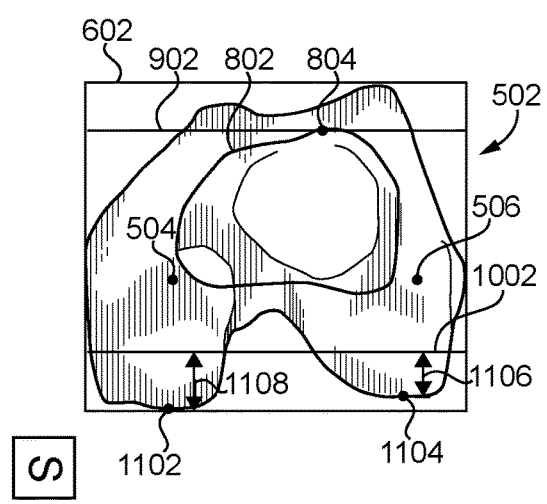
FIG. 11C

1200

| LEGION PRIMARY SIZE | CONSERVATIVE | | STANDARD | | AGGRESSIVE | |
|---|---|---|---|---|---|---|
| | LOWER BOUNDARY | UPPER BOUNDARY | LOWER BOUNDARY | UPPER BOUNDARY | LOWER BOUNDARY | UPPER BOUNDARY |
| 2 | 49.809 | 50.809 | 49.809 | 52.809 | 52.809 | 57.809 |
| 3 | 52.197 | 53.197 | 52.197 | 55.197 | 55.197 | 60.197 |
| 4 | 54.813 | 55.813 | 54.813 | 57.813 | 57.813 | 62.813 |
| 5 | 57.125 | 58.125 | 57.125 | 60.125 | 60.125 | 65.125 |
| 6 | 59.157 | 60.157 | 59.157 | 62.157 | 62.157 | 67.157 |
| 7 | 60.935 | 61.935 | 60.935 | 63.935 | 63.935 | 68.935 |
| 8 | 62.306 | 63.306 | 62.306 | 65.306 | 65.306 | 70.306 |

| ADDITIONAL FLEXION (DEGREE) | IMPLANT SIZE | | | | | | |
|---|---|---|---|---|---|---|---|
| | 2 | 3 | 4 | 5 | 6 | 7 | 8 |
| 0.00 | 19.68 | 15.61 | 11.58 | 8.08 | 4.62 | 0.57 | 3.93 |
| 0.25 | 19.55 | 15.47 | 11.41 | 7.91 | 4.43 | 0.38 | 4.13 |
| 0.50 | 19.43 | 15.34 | 11.26 | 7.74 | 4.26 | 0.20 | 4.32 |
| 0.75 | 19.31 | 15.20 | 11.10 | 7.57 | 4.08 | 0.01 | 4.51 |
| 1.00 | 19.21 | 15.08 | 10.95 | 7.41 | 3.91 | 0.16 | 4.69 |
| 1.25 | 19.10 | 14.96 | 10.80 | 7.25 | 3.74 | 0.34 | 4.87 |
| 1.50 | 19.00 | 14.83 | 10.65 | 7.09 | 3.58 | 0.51 | 5.05 |
| 1.75 | 18.90 | 14.71 | 10.50 | 6.93 | 3.41 | 0.69 | 5.24 |
| 2.00 | 18.80 | 14.58 | 10.36 | 6.77 | 3.24 | 0.86 | 5.42 |

FIG. 13

PREOPERATIVE FEMORAL IMPLANT SIZING

CROSS-REFERENCE TO RELATED APPLICATIONS

This application claims the benefit of U.S. Provisional Application Ser. No. 62/380,077 filed on Aug. 26, 2016, the contents of which are incorporated herein by reference in their entirety.

BACKGROUND

Total knee arthroplasty generally involves the placement of a femoral implant in a specific orientation. Some patients may fit standard femoral implant sizes, whereas other patients may be ideally fitted to an in-between or custom size. The orientation may be defined with six degrees of freedom: three rotations (flexion-extension, varus-valgus, and internal-external) and three translations (anterior-posterior, distal-proximal, and medial-lateral). Further, the orientation may be determined by measuring anatomical landmarks and features, making visual adjustments, and incorporating surgeon-specific preferences. Oftentimes, an implant manufacturer supplies a sizing apparatus that a surgeon uses to intraoperatively estimate the appropriate femoral implant size. Without knowing the size of the femoral implant in advance of the surgical procedure, a hospital may have to stock femoral implants of all available sizes, which could result in excess inventory.

SUMMARY

In one embodiment, a method may include locating a distal medial condyle, a distal lateral condyle, a posterior medial condyle, and a posterior lateral condyle of a femoral bone model of a distal femur of a patient, and determining a posterior resection plane based on a location of the distal medial condyle, a location of the distal lateral condyle, one or more dimensions of a prospective femoral implant of a selected size, and one or more surgical preferences. The method may further include determining a first distance between the posterior medial condyle and the posterior resection plane and a second distance between the posterior lateral condyle and the posterior resection plane, determining a difference between a target value and an average of the first distance and the second distance, and selecting a desired femoral implant size of a plurality of possible femoral implant sizes based on the determined difference between the target value and the average of the first distance and the second distance determined for each of the plurality of possible femoral implant sizes. The target value may be associated with a thickness of the prospective femoral implant. Further embodiments, forms, features, and aspects of the present application shall become apparent from the description and figures provided herewith.

BRIEF DESCRIPTION OF THE DRAWINGS

The concepts described herein are illustrative by way of example and not by way of limitation in the accompanying figures. For simplicity and clarity of illustration, elements illustrated in the figures are not necessarily drawn to scale. Where considered appropriate, references labels have been repeated among the figures to indicate corresponding or analogous elements.

FIG. 5A is an anterior view of a femoral bone model of a distal femur showing distal medial and distal lateral condyles of the femoral bone model;

FIG. 5B is a lateral view of the femoral bone model of FIG. 5A;

FIG. 5C is a superior view of the femoral bone model of FIG. 5A;

FIG. 11A is an anterior view of the femoral bone model showing posterior medial and posterior lateral condyles of the femoral bone model;

FIG. 11B is a lateral view of the femoral bone model of FIG. 11A;

FIG. 11C is a superior view of the femoral bone model of FIG. 11A;

FIG. 12 is a simplified diagram of at least one embodiment of a table of offsets of the cortex plane relative to the primary plane; and FIG. 13 is a simplified diagram of at least one embodiment of a sample table of resultant differences determined based on the techniques described herein.

DETAILED DESCRIPTION OF THE DRAWINGS

Figure 1:
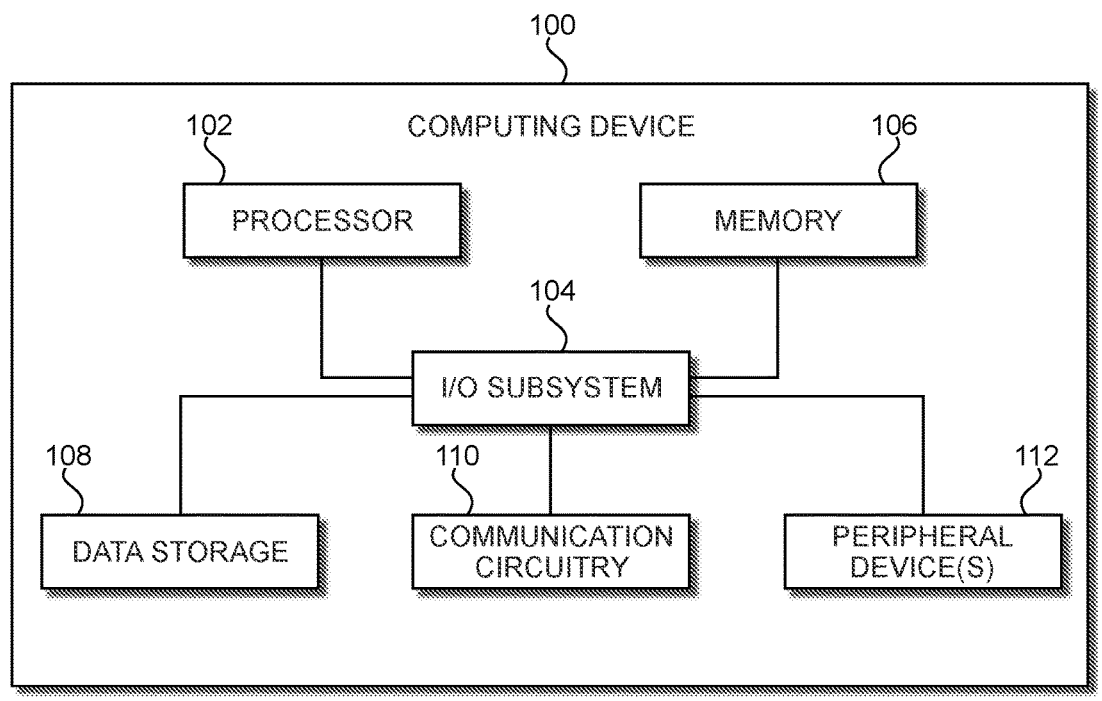
FIG. 1 is a simplified block diagram of at least one embodiment of a computing device for preoperative femoral component sizing.

Although the concepts of the present disclosure are susceptible to various modifications and alternative forms, specific embodiments have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described. Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

The disclosed embodiments may, in some cases, be implemented in hardware, firmware, software, or a combination thereof. The disclosed embodiments may also be implemented as instructions carried by or stored on one or more transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, in the illustrative embodiment, a computing device 100 for preoperative femoral implant sizing is shown. As described in detail below, the computing device 100 analyzes a femoral bone model of a distal femur of a patient to determine an appropriate size of a prospective femoral implant for a contemplated surgical procedure (e.g., a total knee arthroplasty). It should be appreciated that, in some embodiments, the techniques described herein eliminate or reduce the need for surgeons to rely on intraoperative measuring guides to ascertain the appropriate femoral implant size. Instead, in the illustrative embodiments, the computing device 100 may automatically or semi-automatically ascertain the appropriate femoral implant size in advance of the surgical procedure while incorporating surgical preferences and/or other parameters into the determination.

The computing device 100 may be embodied as any type of computing device capable of performing the functions described herein. For example, the computing device 100 may be embodied as a desktop computer, laptop computer, tablet computer, notebook, netbook, Ultrabook™, cellular phone, smartphone, wearable computing device, personal digital assistant, mobile Internet device, Internet of Things (IoT) device, server, router, switch, and/or any other computing/communication device capable of performing the functions described herein. As shown in FIG. 1, the illustrative computing device 100 includes a processor 102, an input/output ("I/O") subsystem 104, a memory 106, a data storage 108, a communication circuitry 110, and one or more peripheral devices 112. Of course, the computing device 100 may include other or additional components, such as those commonly found in a typical computing device (e.g., various input/output devices and/or other components), in other embodiments. Additionally, in some embodiments, one or more of the illustrative components may be incorporated in, or thereof, may be incorporated in the processor 102 in some embodiments. Although a single computing device 100 is illustratively shown, it should be appreciated that one or more of the components of the computing device 100 described herein may be distributed across multiple computing devices. In other words, the techniques described herein may be employed by a computing system that includes one or more computing devices.

The processor 102 may be embodied as any type of processor capable of performing the functions described herein. For example, the processor 102 may be embodied as a single or multi-core processor(s), digital signal processor, microcontroller, or other processor or processing/controlling circuit. Similarly, the memory 106 may be embodied as any type of volatile or non-volatile memory or data storage capable of performing the functions described herein. In operation, the memory 106 may store various data and software used during operation of the computing device 100 such as operating systems, applications, programs, libraries, and drivers. The memory 106 is communicatively coupled to the processor 102 via the I/O subsystem 104, which may be embodied as circuitry and/or components to facilitate input/output operations with the processor 102, the memory 106, and other components of the computing device 100. For example, the I/O subsystem 104 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 104 may form a portion of a system-on-a-chip (SoC) and be incorporated, along with the processor 102, the memory 106, and other components of the computing device 100, on a single integrated circuit chip.

The data storage 108 may be embodied as any type of device or devices configured for short-term or long-term storage of data such as, for example, memory devices and circuits, memory cards, hard disk drives, solid-state drives, or other data storage devices. The data storage 108 and/or the memory 106 may store various data during operation of the computing device 100 useful for performing the functions described herein.

The communication circuitry 110 may be embodied as any communication circuit, device, or collection thereof, capable of enabling communications between the computing device 100 and other remote devices over a network (not shown). The communication circuitry 110 may be configured to use any one or more communication technologies (e.g., wireless or wired communications) and associated protocols (e.g., Ethernet, Bluetooth®, Wi-Fi®, etc.) to effect such communication.

The peripheral devices 112 may include any number of additional peripheral or interface devices, such as speakers, microphones, additional storage devices, and so forth. The particular devices included in the peripheral devices 112 may depend on, for example, the type and/or intended use of the computing device 100. For example, in some embodiments, the peripheral devices 112 may include a keyboard, mouse, display, touchscreen display, printer, alarm, status indicator, handheld device, diagnostic tool, reader device, and/or one or more other suitable peripheral devices.

Figure 2:
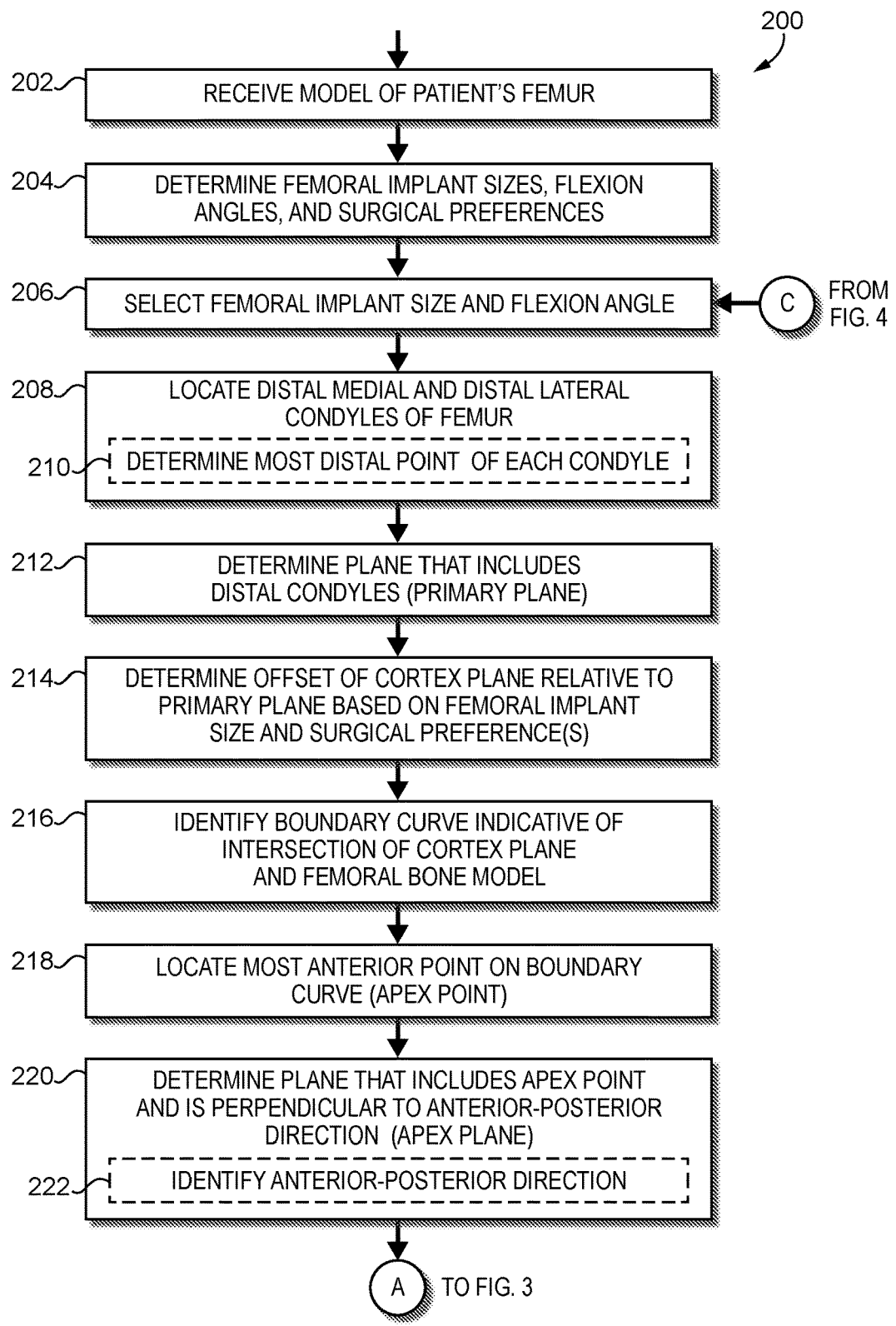
FIGS. 2-4 are a simplified flow diagram of at least one embodiment of a method for preoperative femoral component sizing that may be executed by the computing device of FIG. 1.
Figure 3:
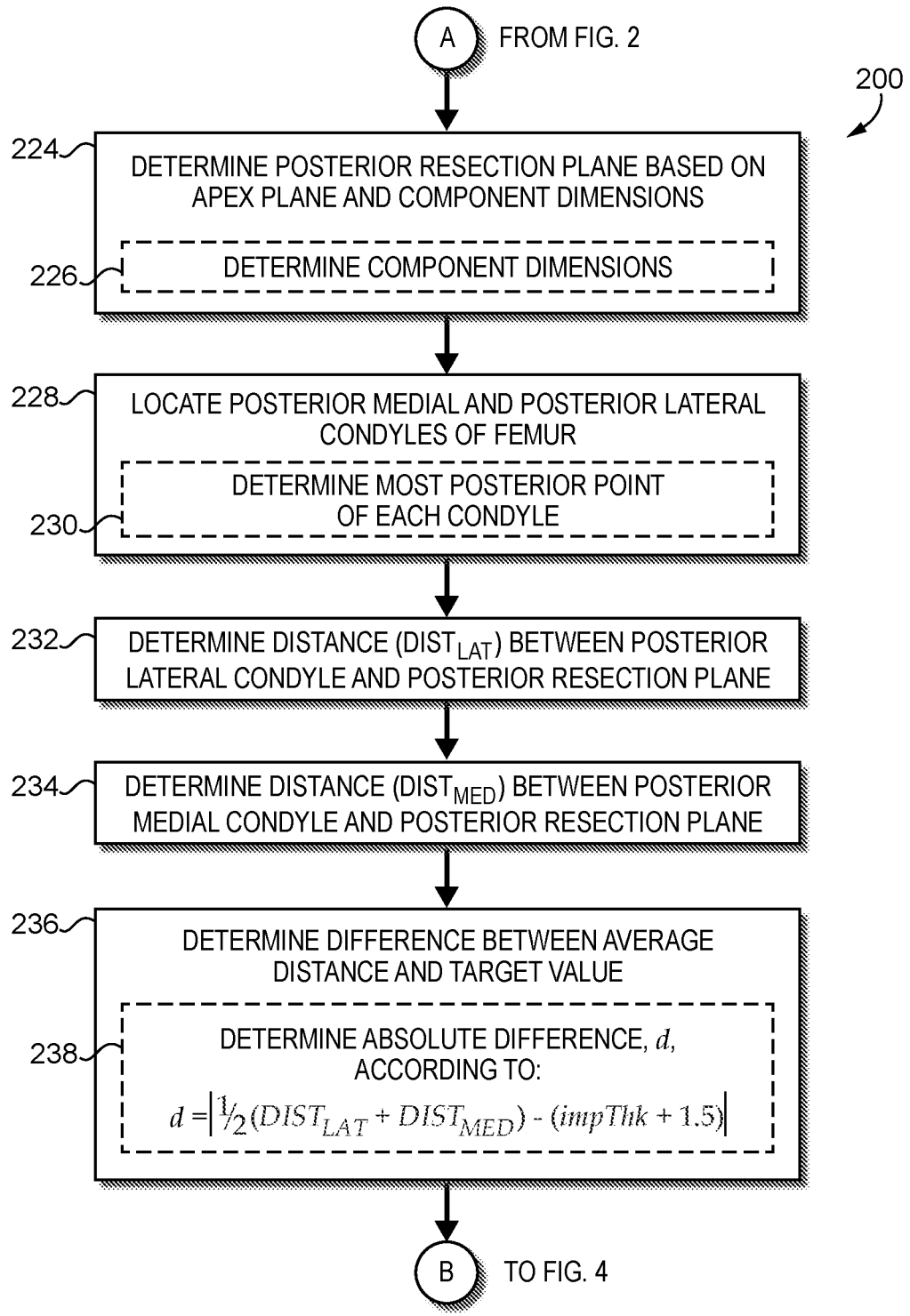
Figure 4:
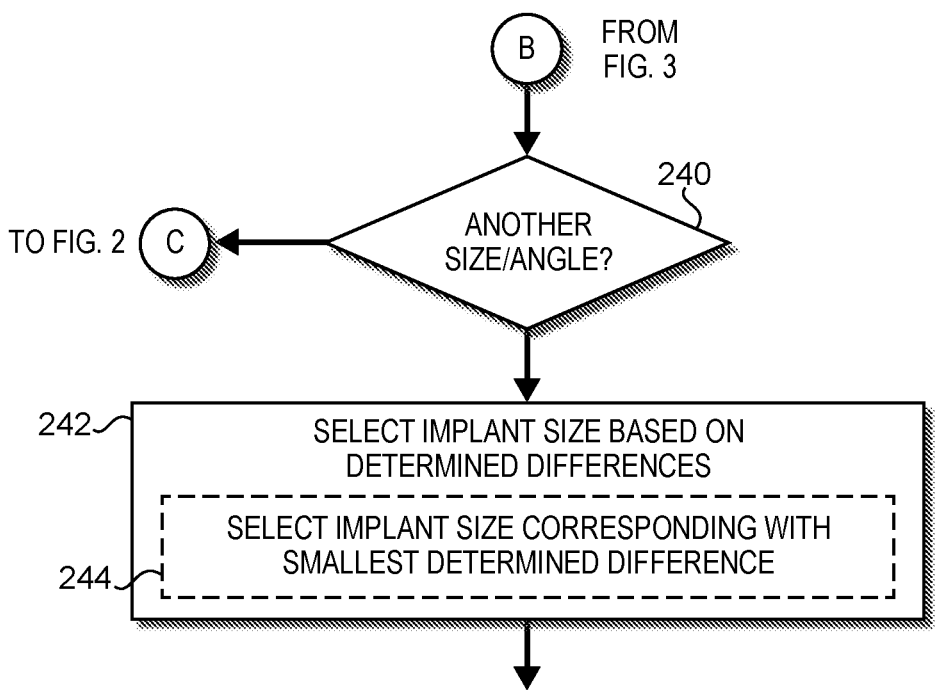

Referring to FIGS. 2-4, in use, the computing device 100 may execute a method 200 for preoperative femoral implant sizing. That is, in the illustrative embodiment, the computing device 100 may preoperatively determine the appropriate size of a prospective femoral implant/component to utilize on a patient in a surgical operation. The illustrative method 200 begins with block 202 in which the computing device 100 receives a femoral bone model 502 of a distal femur of a patient. For example, the computing device 100 may retrieve the femoral bone model 502 from the memory 106 or data storage 108 of the computing device 100 or receive the femoral bone model 502 from a peripheral device 112 or remote computing device depending on the particular embodiment. In the illustrative embodiment, the femoral bone model 502 is a three-dimensional bone model of a distal portion of a patient's femur generated from suitable preoperative diagnostic data such as, for example, one or more X-ray images, magnetic resonance images ("MRI"), computer tomography ("CT") images, and/or other suitable diagnostic data. It should be appreciated that, in some embodiments, the femoral bone model 502 may be generated from the preoperative diagnostic data using one or more computer aided design ("CAD") systems or other model-generating systems. For example, common CAD systems known in the art include SolidWorks® (produced by SolidWorks Corporation, 300 Baker Avenue, Concord, Mass. 01742) and Pro Engineer® (produced by Parametric Technology Corporation, 140 Kendrick Street, Needham, Mass. 02494). In some embodiments, one or more CAD systems or other model-generating systems may generate a three-dimensional bone model of the patient's femur having three degrees of freedom in orientation based on such images and/or diagnostic data. It should be appreciated that, in the illustrative embodiment, the femoral bone model 502 includes adequate information (e.g., anatomical landmarks and features) for preoperative estimation of the proper femoral implant size and allows for the application of one or more surgeon-specific surgical preferences in the sizing determination.

As described below, the computing device 100 identifies the location of various features of the femoral bone model 502 and identifies/defines various geometrical features (e.g., points, lines, planes, etc.) based on the femoral bone model 502. It should be appreciated that the particular techniques, algorithms, and/or mechanisms for doing so may vary depending on the particular embodiment. For example, in some embodiments, edge detection algorithms (e.g., Canny edge detection, Sobel filters, etc.), image segmentation algorithms (e.g., pyramid segmentation, watershed segmentation, etc.), blob detection algorithms, feature identification and/or matching algorithms (e.g., SIFT, SURF, etc.), and/or other suitable algorithms may be used to analyze the femoral bone model 502 and/or representations of (or based on) the femoral bone model 502. In some embodiments, it should be appreciated that rather than analyzing the femoral bone model 502 itself, the computing device 100 may analyze two-dimensional images from one or more perspectives. For example, as described above, in the illustrative embodiment, the computing device 100 may analyze two-dimensional images representative of an anterior view, lateral/right view, and superior view of the femoral bone model 502.

In block 204, the computing device 100 determines the possible femoral implant sizes of a prospective femoral implant (e.g., an implant type selected by a surgeon), the additional allowable flexion or range of flexion permitted, and one or more surgical preferences (e.g., surgeon-defined preferences). Depending on the particular embodiment, the computing device 100 may make such determinations based on stored data (e.g., a surgical profile) and/or user input. In an embodiment, the computing device 100 may determine that a particular prospective femoral implant is available in sizes 2-8 (e.g., standard, primary, or non-custom sizes) and that 0-2 degrees of additional flexion is permitted. Additionally, the computing device 100 may determine various surgical preferences including, for example, whether the surgeon prefers a conservative, standard, or aggressive anterior resection, whether the surgeon prefers a conservative, standard, or aggressive distal resection (i.e., associated with the implant thickness), whether the surgeon prefers to downsize or upsize for between-size measurements/decisions, and/or other surgical preferences. In some embodiments, the range of additional flexion permitted may be a surgeon-specified surgical preference.

In block 206, the computing device 100 selects a size and flexion angle of the possible femoral implant size and permitted flexion angles. In some embodiments, it should be appreciated that the range of permitted additional flexion may be expressed discretely (e.g., in steps). For example, in the example described above in which 0-2 degrees of additional flexion is permitted, the flexion angles from which to choose may be expressed in 0.25 degree steps (i.e., 0.00 degrees, 0.25 degrees, 0.50 degrees, 0.75 degrees, 1.00 degrees, 1.25 degrees, 1.50 degrees, 1.75 degrees, and 2.00 degrees). Further, the step size may vary depending on the particular embodiment. For example, in another embodiment, the 0-2 degrees of permitted additional flexion may be expressed in 0.50 degree steps (i.e., 0.00 degrees, 0.50 degrees, 1.00 degrees, 1.50 degrees, and 2.00 degrees). As described below, the computing device 100 may similarly analyze multiple (e.g., every) combination of possible femoral implant size and permitted flexion angle. As such, the computing device 100 may select the size and flexion angle according to any suitable scheme consistent with the techniques described herein.

As indicated above, the femoral bone model 502 includes features mimicking and/or otherwise representative of anatomical features a distal femur of a patient. As such, referring to FIGS. 5A-C, the femoral bone model 502 includes a distal end 508 and a proximal end 510. Similarly, the femoral bone model 502 includes a medial side 512, a lateral side 514, an anterior side 516, and a posterior side 518. Further, the femoral bone model 502 includes a medial condyle 520, a lateral condyle 522, and an intercondylar region 524 including a trochlear groove 526 and a trochlear notch 528. Referring back to FIG. 2, in block 208, the computing device 100 locates the distal medial condyle 504 and the distal lateral condyle 506 of the femoral bone model 502 as shown in FIGS. 5A-C. In particular, in block 210, the computing device 100 may locate the most distal point of each condyle in some embodiments. That is, the computing device 100 may locate the distal-most point of the distal medial condyle 504 and the distal-most point of the distal lateral condyle 506.

Figure 6A:
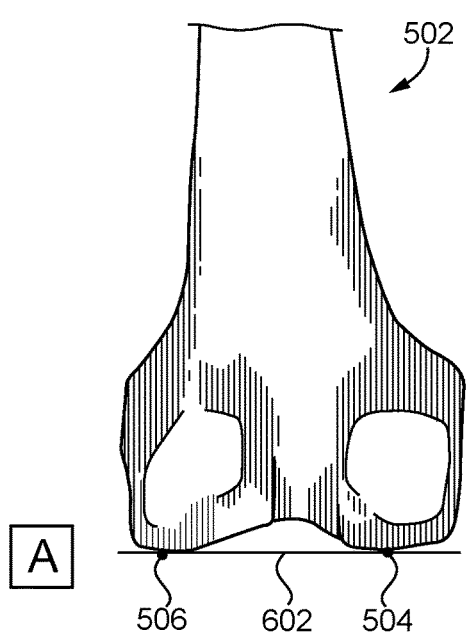
FIG. 6A is an anterior view of the femoral bone model showing a primary plane.
Figure 6B:
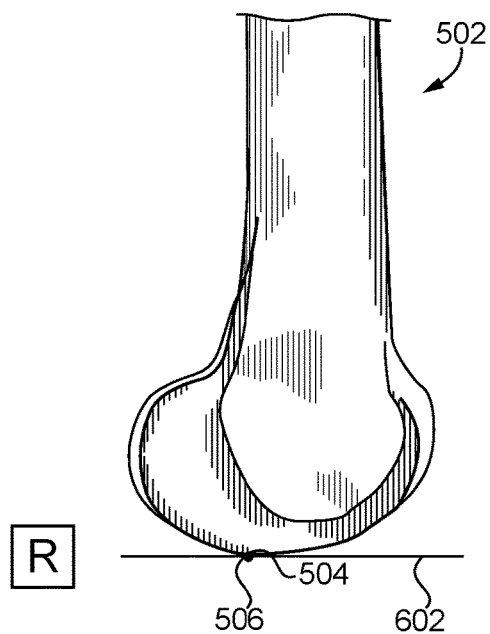
FIG. 6B is a lateral view of the femoral bone model of FIG. 6A.
Figure 6C:
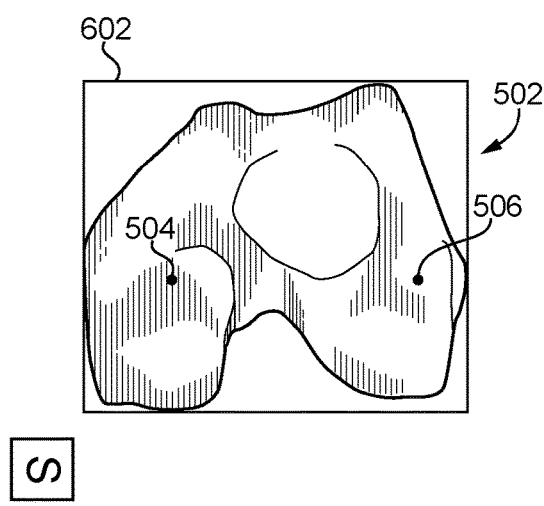
FIG. 6C is a superior view of the femoral bone model of FIG. 6A.
Figures 7A, 7B:
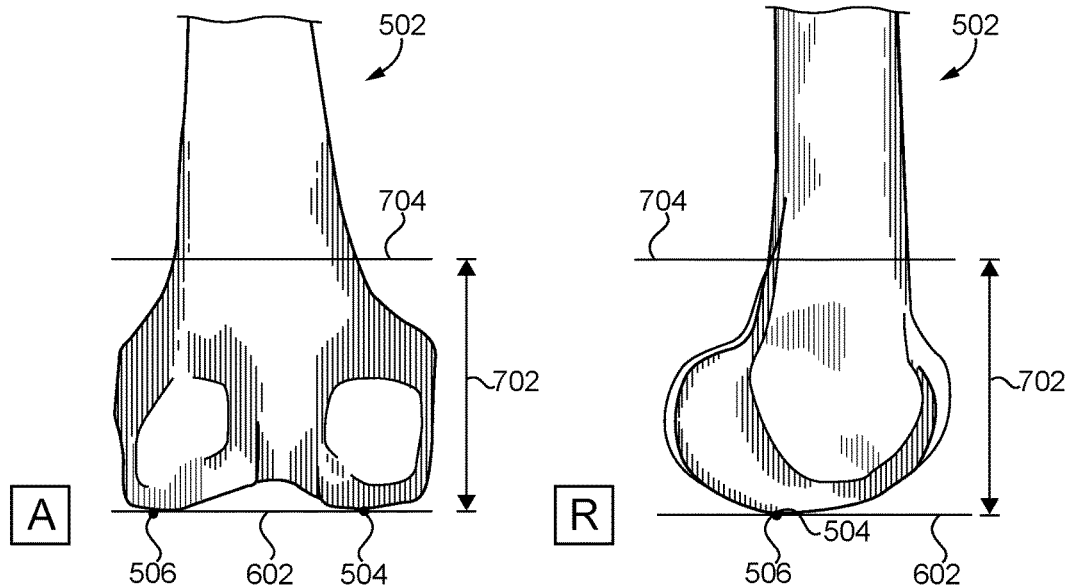
FIG. 7A is an anterior view of the femoral bone model showing a cortex plane.
FIG. 7B is a lateral view of the femoral bone model of FIG. 7A.
Figure 7C:
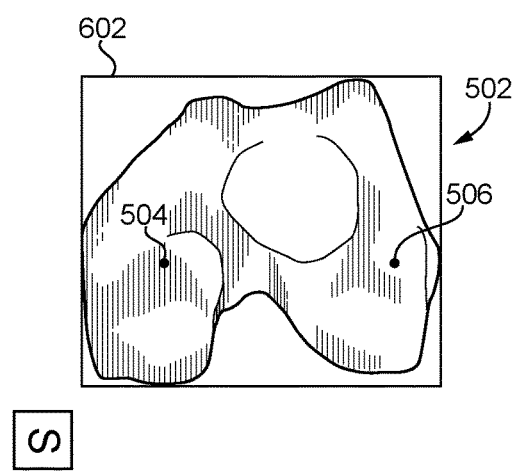
FIG. 7C is a superior view of the femoral bone model of FIG. 7A.

In block 212, the computing device 100 determines a primary reference plane 602 that includes the distal medial condyle 504 and the distal lateral condyle 506 as shown in FIGS. 6A-C. For simplicity, the primary reference plane 602 may hereinafter be referred to simply as the primary plane 602. It should be appreciated that, in some embodiments, the primary plane 602 passes through the distal-most points of the medial condyle 520 and the lateral condyle 522. In block 214, the computing device 100 determines an offset 702 (e.g., the height) of a cortex plane 704 relative to the primary plane 602 based on the selected femoral implant size and the surgical preferences as shown in FIGS. 7A-C. In the illustrative embodiment, the cortex plane 704 is parallel to the primary plane 602 and the offset 702 indicates the distance between the cortex plane 704 and the primary plane 602. As such, it should be appreciated that, in some embodiments, the cortex plane 704 may located or defined by translating the primary plane 602 superiorly by a distance defined by the offset 702. It should be appreciated that the computing device 100 may determine the offset 702 using any suitable technique, algorithm, and/or mechanism. In the illustrative embodiment, the computing device 100 may analyze one or more tables or other data structures that identify an appropriate offset based on the selected femoral implant size and the surgical preferences. For example, the table 1200 shown in FIG. 12 identifies several sizes of a prospective femoral component (i.e., sizes 2-8) from the example referenced above and corresponding offsets 702 depending on whether the surgeon prefers conservative, standard, or aggressive resection (e.g., anterior resection). In the example described above, the surgical preferences may include an aggressive anterior resection, a standard distal resection (e.g., associated with the implant thickness), and to downsize for between-size measurements/decisions. Further, as indicated above, the surgeon may preference an additional 0-2 degrees of allowable flexion (e.g., in 0.25 degree increments). In such an embodiment, it should be appreciated that the computing device 100 determines an offset 702 of 67.157 millimeters between the cortex plane 704 and the primary plane 602. In some embodiments, flexion may only be used when allowed by the surgeon to assist with determining proper sizing of the implant. The value may be determined based on the techniques described below (e.g., based on the location of the implant position).

Figure 8A:
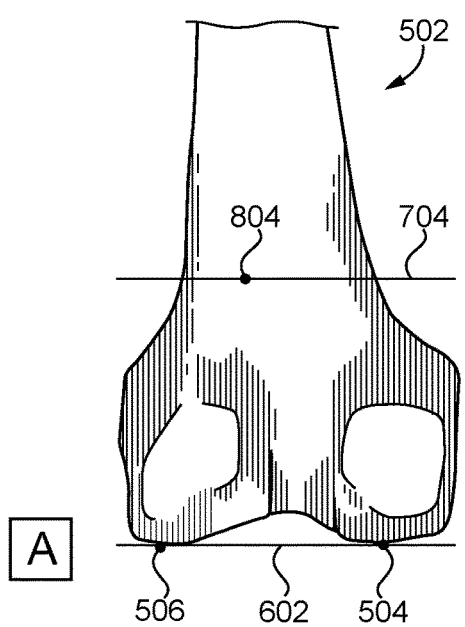
FIG. 8A is an anterior view of the femoral bone model showing a boundary curve and an apex point of the boundary curve.
Figure 8B:
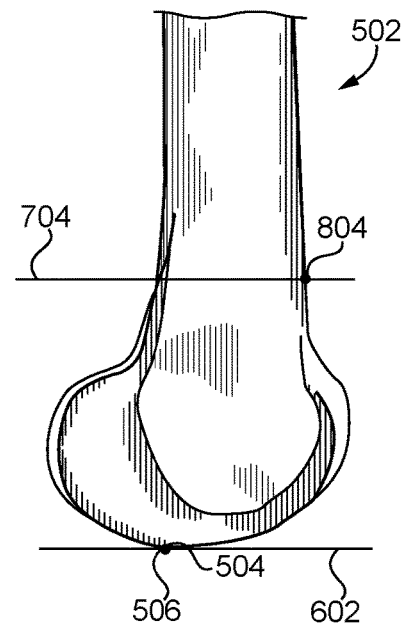
FIG. 8B is a lateral view of the femoral bone model of FIG. 8A.
Figure 8C:
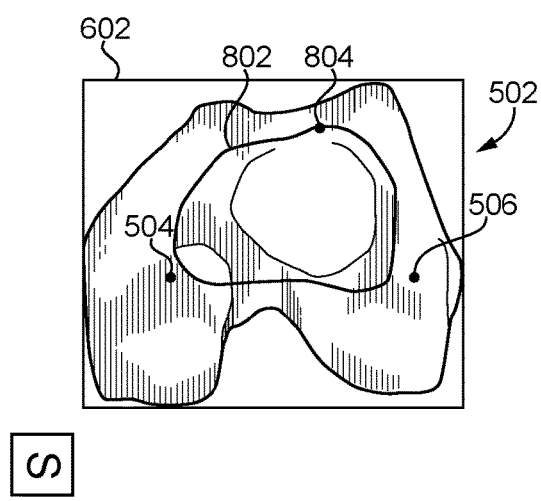
FIG. 8C is a superior view of the femoral bone model of FIG. 8A.
Figures 9A, 9B:
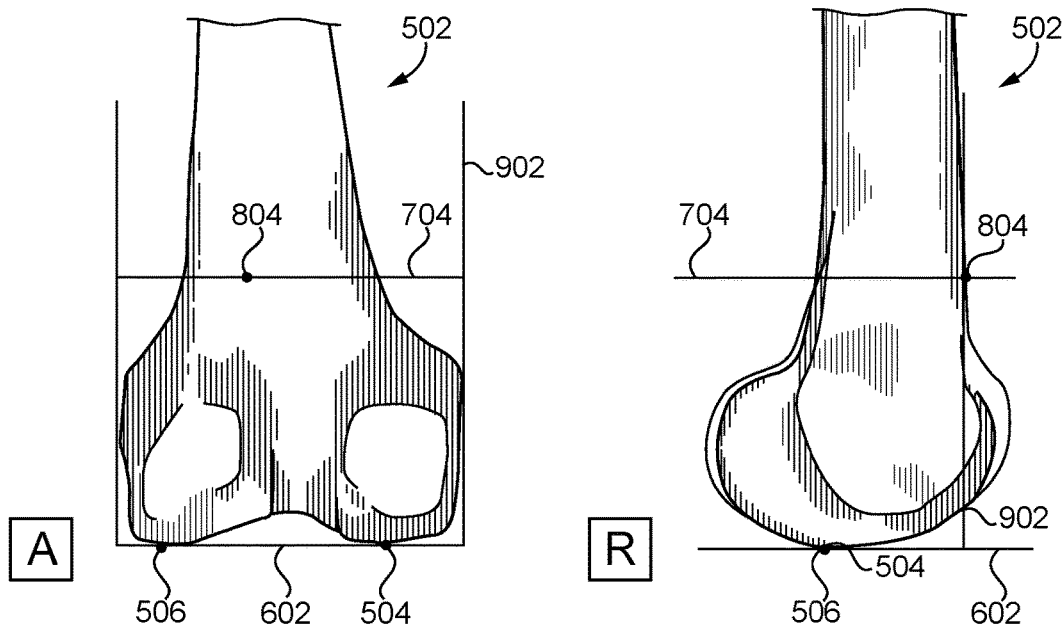
FIG. 9A is an anterior view of the femoral bone model showing an apex plane.
FIG. 9B is a lateral view of the femoral bone model of FIG. 9A.
Figure 9C:
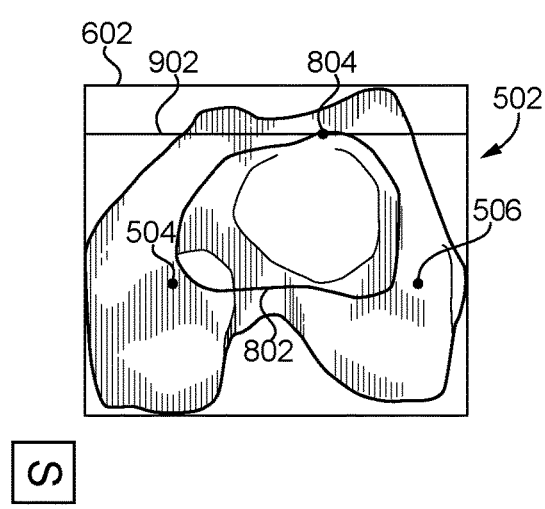
FIG. 9C is a superior view of the femoral bone model of FIG. 9A.

In block 216, the computing device 100 identifies a boundary curve 802 indicative of an intersection of the cortex plane 704 and the femoral bone model 502 as shown in FIGS. 8A-C. In particular, in the illustrative embodiment, the computing device 100 determines the boundary curve 802 that defines an intersection of the cortex plane 704 and an outer boundary of a cross section of the femoral bone model 502 taken at the cortex plane 704. In block 218, the computing device 100 locates an anterior point (i.e., an apex point 804) of the boundary curve 802. More specifically, in some embodiments, the apex point 804 is the anterior-most point on the boundary curve 802. In block 220, the computing device 100 determines an apex plane 902 that includes the apex point 804 and is perpendicular to an anterior-posterior direction as shown in FIGS. 9A-C. In other words, in the illustrative embodiment, the apex plane 902 is perpendicular to the cortex plane 704 and the primary plane 602 and includes an anterior point (e.g., an anterior-most point) of the boundary curve 802. In determining the apex plane 902, in block 222, the computing device 100 may identify the anterior-posterior direction. It should be appreciated that the computing device 100 may utilize any suitable techniques, algorithms, and/or mechanisms to do so. For example, in some embodiments, the femoral bone model 502 may include various directions predefined relative to a suitable reference point.

Figures 10A, 10B:
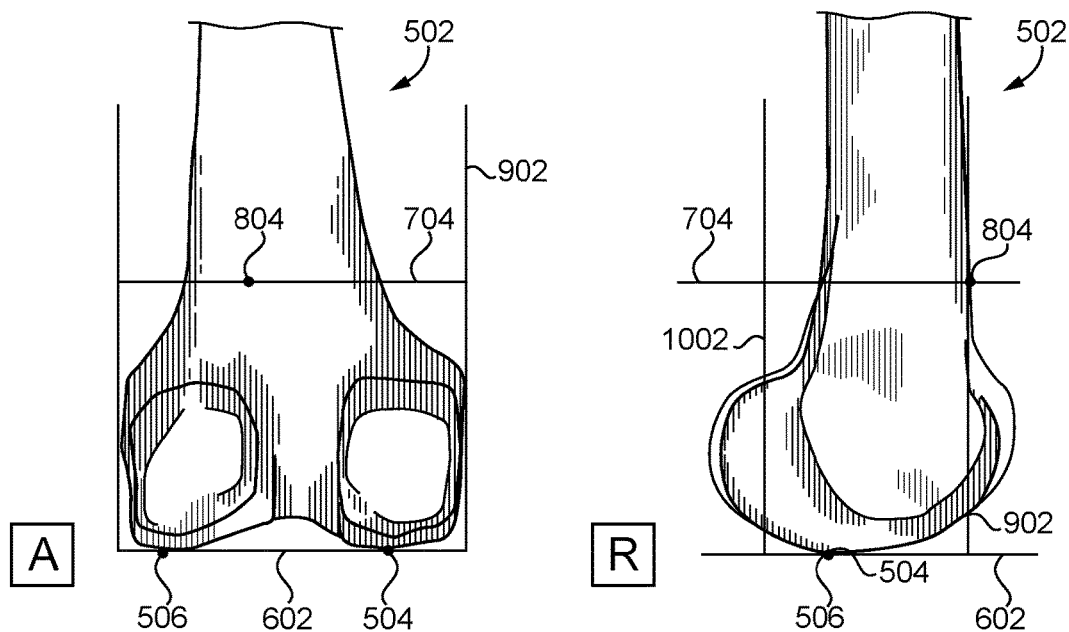
FIG. 10A is an anterior view of the femoral bone model showing a posterior resection plane.
FIG. 10B is a lateral view of the femoral bone model of FIG. 10A.
Figure 10C:
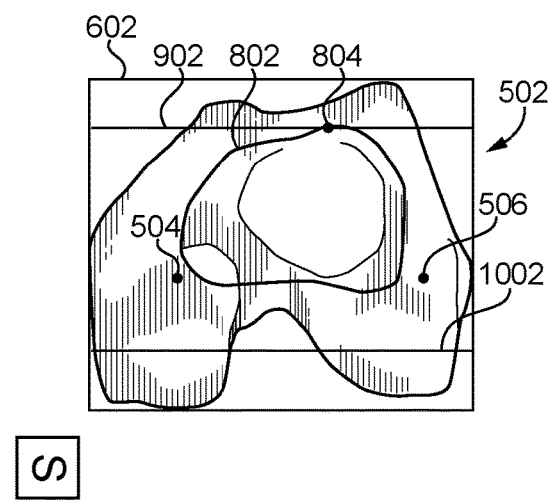
FIG. 10C is a superior view of the femoral bone model of FIG. 10A.

In block 224 of FIG. 3, the computing device 100 determines a posterior resection plane 1002 based on the apex plane 902 and one or more dimensions of the prospective femoral implant of the selected size as shown in FIGS. 10A-C. In doing so, in block 226, the computing device 100 may determine the dimensions of the prospective femoral implant of the selected size. For example, in some embodiments, the computing device 100 may store data indicating various dimensions and/or other relevant parameters of the prospective femoral implant for each of the possible femoral implant sizes. In particular, in some embodiments, the computing device 100 may determine an offset distance of the posterior resection plane 1002 from the apex plane 902 based on the component dimensions such that the posterior resection plane 1002 may be located by translating the apex plane 902 the determined offset distance in a posterior direction. In some embodiments, the offset distance may be determined based, for example, on a lookup table, which may correlate implant size with offset distance. For example, component size may change as the posterior, anterior, and/or other dimensions change.

In block 228, the computing device 100 locates the posterior medial condyle 1102 and the posterior lateral condyle 1104 of the femoral bone model 502 as shown in FIGS. 11A-C. In particular, in block 230, the computing device 100 may locate the most posterior point of each condyle in some embodiments. That is, the computing device 100 may locate the posterior-most point of the posterior medial condyle 1102 and the posterior-most point of the posterior lateral condyle 1104. In block 232, the computing device 100 determines the distance 1106 ($DIST_{LAT}$) between the posterior lateral condyle 1104 and the posterior resection plane 1002. Similarly, in block 234, the computing device 100 determines the distance 1108 ($DIST_{MED}$) between the posterior medial condyle 1102 and the posterior resection plane 1002. In some embodiments, the distance 1106 is the shortest distance between the posterior lateral condyle 1104 and the posterior resection plane 1002 and/or the distance 1108 is the shortest distance between the posterior medial condyle 1102 and the posterior resection plane 1002. In some embodiments, the distance 1106 is the distance between the posterior lateral condyle 1104 and the posterior resection plane 1002 measured in a direction perpendicular to the posterior resection plane 1002 and/or the distance 1108 is the distance between the posterior medial condyle 1102 and the posterior resection plane 1002 measured in a direction perpendicular to the posterior resection plane 1002.

In block 236, the computing device 100 compares the distance 1106 ($DIST_{LAT}$) and the distance 1108 ($DIST_{MED}$) or a value derived based on a function of the distances 1006, 1008 to a target value based on the thickness of the prospective femoral implant (e.g., a dimension of the implant in a superior-inferior direction when implanted). In particular, in some embodiments, the computing device 100 may determine the difference (e.g., an absolute distance) between the target value and the average of the distance 1106 ($DIST_{LAT}$) and the distance 1108 ($DIST_{MED}$). For example, the computing device 100 may determine the difference, d, according to $d=|\frac{1}{2}(DIST_{LAT}+DIST_{MED})-(impThk+1.5\ mm)|$, wherein impThk is the implant thickness. In such an embodiment, it should be appreciated that the target value is equal to (impThk+1.5 mm), the implant thickness plus a 1.5 millimeter offset. In other embodiments, another suitable target value may employed based on the techniques described herein (e.g., using a different offset). In other embodiments, the computing device 100 may utilize another suitable measurement of the difference. For example, in some embodiments, the difference may be determined according to $d=(\frac{1}{2}(DIST_{LAT}+DIST_{MED})-(impThk+1.5\ mm)^2$ or another measurement consistent with the techniques described herein.

In the illustrative embodiment, the determined difference is stored in a table or other suitable data structure and associated with the selected implant size and amount of additional flexion such as, for example, the table 1300 of FIG. 13. It should be appreciated that each entry of the table 1300 identifies a difference computed based on the techniques described above for the corresponding selected implant size and additional flexion angle.

In block 240 of FIG. 4, the computing device 100 determines whether to select another possible combination of size and flexion angle. As described above, the computing device 100 determines the possible femoral implant sizes and additional permitted flexion angles (see, for example, block 204 of FIG. 2). In the illustrative embodiment, the computing device 100 applies the techniques described above to determine a difference (or other suitable reference number) for each combination of femoral implant size and flexion angle as shown by way of example in the table 1300 of FIG. 13. Accordingly, if the computing device 100 determines that a difference has not been determined for one or more such combinations, the method 200 returns to block 206 of FIG. 2 in which the computing device 100 selects a size and flexion angle of the possible femoral implant sizes and permitted flexion angles for which a difference has not yet already been determined.

However, if the computing device 100 determines that all such values have been determined (i.e., a table similar to the table 1300 or another suitable data structure is complete), the method 200 advances to block 242 of FIG. 4 in which the computing device 100 selects a desired (e.g., optimal) implant size based on the determined differences (e.g., identified in an equivalent of the table 1300). For example, in block 244, the computing device 100 may select the femoral implant size corresponding with the smallest determined difference (e.g., the smallest value in the table 1300). In embodiments in which there are multiple femoral implant sizes having the same associated smallest determined difference, the computing device 100 may employ one or more of the surgical preferences described above to select the desired implant size. In some embodiments, the computing device 100 utilizes the surgeon's upsize/downsize preference for between-size decisions/measurements to select the desired femoral implant size. For example, if the computing device 100 determined that an upsize preference was specified, the computing device 100 may select the larger of the femoral implant sizes having the same associated smallest difference.

It should be appreciated that the techniques described herein may result in the preoperative selection of the most optimal femoral implant size. That is, the surgeon may use the prospective femoral implant of the preoperatively selected implant size to perform a surgical procedure on the patient with a greater degree of confidence in the implant size than when using conventional implant sizing techniques. For example, the surgeon may resect the distal femur of the patient in preparation for attachment of the prospective femoral implant by a corresponding amount with confidence that the femoral implant of the selected size with fit and function as intended.

In one embodiment, a method comprises locating, by a computing system, a distal medial condyle, a distal lateral condyle, a posterior medial condyle, and a posterior lateral condyle of a femoral bone model of a distal femur of a patient; determining, by the computing system, a posterior resection plane based on a location of the distal medial condyle, a location of the distal lateral condyle, one or more dimensions of a prospective femoral implant of a selected size, and one or more surgical preferences; determining, by the computing system, a first distance between the posterior medial condyle and the posterior resection plane and a second distance between the posterior lateral condyle and the posterior resection plane; determining, by the computing system, a difference between a target value and an average of the first distance and the second distance, wherein the target value is associated with a thickness of the prospective femoral implant; and selecting, by the computing system, a desired femoral implant size of a plurality of possible femoral implant sizes based on the determined difference between the target value and the average of the first distance and the second distance determined for each of the plurality of possible femoral implant sizes.

In some embodiments, determining the posterior resection plane comprises determining a primary plane that includes the distal medial condyle and the distal lateral condyle; determining an offset of a cortex plane relative to the primary plane based on the selected size and the one or more surgical preferences; identifying a boundary curve indicative of an intersection of the cortex plane and the femoral bone model; locating an apex point of the boundary curve, wherein the apex point is an anterior-most point of the boundary curve; determining an apex plane that includes the apex point and is perpendicular to an anterior-posterior direction; and determining a posterior resection plane based on the apex plane and the one or more dimensions of the prospective femoral implant of the selected size.

In some embodiments, determining the primary plane comprises determining a plane that includes a first distal-most point of the distal medial condyle and a second distal-most point of the distal lateral condyle.

In some embodiments, the apex point is an anterior-most point of the boundary curve.

In some embodiments, selecting the desired femoral implant size comprises selecting a femoral implant size of the plurality of possible femoral implant sizes associated with a smallest determined difference between the target value and the average of the first distance and the second distance.

In some embodiments, determining the difference between the target value and the average of the first distance and the second distance comprises determining the difference, d, according to $d=|\frac{1}{2}(DIST_{LAT}+DIST_{MED})-(impThk+1.5\ mm)|$, wherein $DIST_{MED}$ is the first distance; wherein $DIST_{LAT}$ is the second distance; and wherein impThk is the thickness of the prospective femoral implant.

In some embodiments, selecting the desired femoral implant size comprises selecting a desired femoral implant size based on the determined difference between the target value and the average of the first distance and the second distance determined for each of the plurality of possible femoral implant sizes and each of a plurality of permitted flexion angles.

In some embodiments, selecting the desired femoral implant size comprises selecting a most optimal femoral implant size of the plurality of possible femoral implant sizes.

In some embodiments, the method may further comprise receiving, by the computing system, model data indicative of the femoral bone model; determining, by the computing system, the plurality of possible femoral implant sizes of the prospective femoral implant and a plurality of permitted flexion angles of the prospective femoral implant; and selecting, by the computing system, a size of the plurality of possible femoral implant sizes and a flexion angle of the plurality of permitted flexion angles, wherein determining the posterior resection plane comprises determining a posterior resection plane based on one or more dimensions of the prospective femoral implant of the selected size of the plurality of possible femoral implant sizes; and wherein selecting the desired femoral implant size comprises selecting a desired femoral implant size based on the determined difference between the target value and the average of the first distance and the second distance determined for each of the plurality of possible femoral implant sizes and each of the plurality of permitted flexion angles.

In some embodiments, the one or more surgical preferences comprise at least one of an anterior resection preference, a distal resection preference, or a maximum permitted flexion angle.

In some embodiments, determining the first distance between the posterior medial condyle and the posterior resection plane comprises determining a first distance between a posterior-most point of the posterior medial condyle and the posterior resection plane; and determining the second distance between the posterior lateral condyle and the posterior resection plane comprises determining a second distance between a posterior-most point of the posterior lateral condyle and the posterior resection plane.

In some embodiments, the method may further comprise performing a surgical procedure on the patient using the prospective femoral implant of the desired femoral implant size.

In some embodiments, the method may further comprise resecting the distal femur of the patient in preparation for attachment of the prospective femoral implant of the desired femoral implant size to the resected distal femur of the patient.

In another embodiment, a computing system comprises at least one processor; and at least one memory comprising a plurality of instructions stored thereon that, in response to execution by the at least one processor, causes the computing system to locate a distal medial condyle, a distal lateral condyle, a posterior medial condyle, and a posterior lateral condyle of a femoral bone model of a distal femur of a patient; determine a posterior resection plane based on a location of the distal medial condyle, a location of the distal lateral condyle, one or more dimensions of a prospective femoral implant of a selected size, and one or more surgical preferences; determine a first distance between the posterior medial condyle and the posterior resection plane and a second distance between the posterior lateral condyle and the posterior resection plane; determine a difference between a target value and an average of the first distance and the second distance, wherein the target value is associated with a thickness of the prospective femoral implant; and select a desired femoral implant size of a plurality of possible femoral implant sizes based on the determined difference between the target value and the average of the first distance and the second distance determined for each of the plurality of possible femoral implant sizes.

In some embodiments, to determine the posterior resection plane comprises to determine a primary plane that includes the distal medial condyle and the distal lateral condyle; determine an offset of a cortex plane relative to the primary plane based on the selected size and the one or more surgical preferences; identify a boundary curve indicative of an intersection of the cortex plane and the femoral bone model; locate an apex point of the boundary curve, wherein the apex point is an anterior-most point of the boundary curve; determine an apex plane that includes the apex point and is perpendicular to an anterior-posterior direction; and determine a posterior resection plane based on the apex plane and the one or more dimensions of the prospective femoral implant of the selected size.

In some embodiments, to select the desired femoral implant size comprises to select a femoral implant size of the plurality of possible femoral implant sizes associated with a smallest determined difference between the target value and the average of the first distance and the second distance.

In some embodiments, to determine the difference between the target value and the average of the first distance and the second distance comprises to determine the difference, d, according to $d=|\frac{1}{2}(DIST_{LAT}+DIST_{MED})-(impThk+1.5\ mm)|$, wherein $DIST_{MED}$ is the first distance; wherein $DIST_{LAT}$ is the second distance; and wherein impThk is the thickness of the prospective femoral implant.

In another embodiment, one or more machine-readable storage media comprises a plurality of instructions stored thereon that, in response to execution by a computing device, causes the computing device to locate a distal medial condyle, a distal lateral condyle, a posterior medial condyle, and a posterior lateral condyle of a femoral bone model of a distal femur of a patient; determine a primary plane that includes the distal medial condyle and the distal lateral condyle; determine an offset of a cortex plane relative to the primary plane based on the selected size and one or more surgical preferences; identify a boundary curve indicative of an intersection of the cortex plane and the femoral bone model; locate an apex point of the boundary curve, wherein the apex point is an anterior point of the boundary curve; determine an apex plane that includes the apex point and is perpendicular to an anterior-posterior direction; determine a posterior resection plane based on the apex plane and one or more dimensions of the prospective femoral implant of the selected size; determine a first distance between the posterior medial condyle and the posterior resection plane and a second distance between the posterior lateral condyle and the posterior resection plane; determine a difference between a target value and an average of the first distance and the second distance, wherein the target value is associated with a thickness of the prospective femoral implant; and select a desired femoral implant size of the plurality of possible femoral implant sizes based on the determined difference between the target value and the average of the first distance and the second distance determined for each of the plurality of possible femoral implant sizes and each of the plurality of permitted flexion angles.

In some embodiments, to select the desired femoral implant size comprises to select a femoral implant size of the plurality of possible femoral implant sizes associated with a smallest determined difference between the target value and the average of the first distance and the second distance.

In some embodiments, to determine the difference between the target value and the average of the first distance and the second distance comprises to determine the difference, d, according to $d=|\frac{1}{2}(DIST_{LAT}\ DIST_{MED})-(impThk+1.5\ mm)|$, wherein $DIST_{MED}$ is the first distance; wherein $DIST_{LAT}$ is the second distance; and wherein impThk is the thickness of the prospective femoral implant.

What is claimed is:

1. A method of femoral implant sizing in advance of a surgical procedure on a patient's knee, the method comprising:
    preoperatively acquiring an image of a distal femur of the patient;
    generating, by a computing system, a femoral bone model from the image;
    locating, by the computing system, a distal medial condyle, a distal lateral condyle, a posterior medial condyle, and a posterior lateral condyle of the femoral bone model;
    determining, by the computing system, a posterior resection plane based on a location of the distal medial condyle, a location of the distal lateral condyle, one or more dimensions of a prospective femoral implant of a selected size, and one or more surgical preferences;
    determining, by the computing system, a first distance between the posterior medial condyle and the posterior resection plane and a second distance between the posterior lateral condyle and the posterior resection plane;
    determining, by the computing system, a difference between a target value and an average of the first distance and the second distance, wherein the target value is associated with a thickness of the prospective femoral implant; and
    selecting, by the computing system, in advance of the surgical procedure on the patient's knee, a desired femoral implant size of a plurality of possible femoral implant sizes based on the determined difference between the target value and the average of the first distance and the second distance determined for each of the plurality of possible femoral implant sizes.

2. The method of claim 1, wherein determining the posterior resection plane comprises:
    determining a primary plane that includes the distal medial condyle and the distal lateral condyle;
    determining an offset of a cortex plane relative to the primary plane based on the selected size and the one or more surgical preferences;
    identifying a boundary curve indicative of an intersection of the cortex plane and the femoral bone model;
    locating an apex point of the boundary curve, wherein the apex point is an anterior-most point of the boundary curve;
    determining an apex plane that includes the apex point and is perpendicular to an anterior-posterior direction; and
    determining a posterior resection plane based on the apex plane and the one or more dimensions of the prospective femoral implant of the selected size.

3. The method of claim 2, wherein determining the primary plane comprises determining a plane that includes a first distal-most point of the distal medial condyle and a second distal-most point of the distal lateral condyle.

4. The method of claim 2, wherein the apex point is an anterior-most point of the boundary curve.

5. The method of claim 1, wherein selecting the desired femoral implant size comprises selecting a femoral implant size of the plurality of possible femoral implant sizes associated with a smallest determined difference between the target value and the average of the first distance and the second distance.

6. The method of claim 1, wherein determining the difference between the target value and the average of the first distance and the second distance comprises determining the difference, d, according to $d=|\frac{1}{2}(DIST_{LAT}+DIST_{MED})-(impThk+1.5\ mm)|$,
    wherein $DIST_{MED}$ is the first distance;
    wherein $DIST_{LAT}$ is the second distance; and
    wherein impThk is the thickness of the prospective femoral implant.

7. The method of claim 1, wherein selecting the desired femoral implant size comprises selecting a desired femoral implant size based on the determined difference between the target value and the average of the first distance and the second distance determined for each of the plurality of possible femoral implant sizes and each of a plurality of permitted flexion angles.

8. The method of claim 1, wherein selecting the desired femoral implant size comprises selecting a most optimal femoral implant size of the plurality of possible femoral implant sizes.

9. The method of claim 1, further comprising:
    receiving, by the computing system, model data indicative of the femoral bone model;
    determining, by the computing system, the plurality of possible femoral implant sizes of the prospective femoral implant and a plurality of permitted flexion angles of the prospective femoral implant; and
    selecting, by the computing system, a size of the plurality of possible femoral implant sizes and a flexion angle of the plurality of permitted flexion angles,
    wherein determining the posterior resection plane comprises determining a posterior resection plane based on one or more dimensions of the prospective femoral implant of the selected size of the plurality of possible femoral implant sizes; and
    wherein selecting the desired femoral implant size comprises selecting a desired femoral implant size based on the determined difference between the target value and the average of the first distance and the second distance determined for each of the plurality of possible femoral implant sizes and each of the plurality of permitted flexion angles.

10. The method of claim 1, wherein the one or more surgical preferences comprise at least one of an anterior resection preference, a distal resection preference, or a maximum permitted flexion angle.

11. The method of claim 1, wherein determining the first distance between the posterior medial condyle and the posterior resection plane comprises determining a first distance between a posterior-most point of the posterior medial condyle and the posterior resection plane; and
    wherein determining the second distance between the posterior lateral condyle and the posterior resection plane comprises determining a second distance between a posterior-most point of the posterior lateral condyle and the posterior resection plane.

12. The method of claim 1, further comprising performing a surgical procedure on the patient using the prospective femoral implant of the desired femoral implant size.

13. The method of claim 1, further comprising resecting the distal femur of the patient in preparation for attachment of the prospective femoral implant of the desired femoral implant size to the resected distal femur of the patient.

14. A computing system for femoral implant sizing in advance of a surgical procedure on a patient's knee, the computing system comprising:
at least one processor; and
at least one memory comprising a plurality of instructions stored thereon that, in response to execution by the at least one processor, causes the computing system to:
preoperatively acquire at least one image of a distal femur of the patient;
generate a femoral bone model from the at least one image;
locate a distal medial condyle, a distal lateral condyle, a posterior medial condyle, and a posterior lateral condyle of the femoral bone model;
determine a posterior resection plane based on a location of the distal medial condyle, a location of the distal lateral condyle, one or more dimensions of a prospective femoral implant of a selected size, and one or more surgical preferences;
determine a first distance between the posterior medial condyle and the posterior resection plane and a second distance between the posterior lateral condyle and the posterior resection plane;
determine a difference between a target value and an average of the first distance and the second distance, wherein the target value is associated with a thickness of the prospective femoral implant; and
select a desired femoral implant size of a plurality of possible femoral implant sizes, in advance of the surgical procedure on the patient's knee, based on the determined difference between the target value and the average of the first distance and the second distance determined for each of the plurality of possible femoral implant sizes.

15. The computing system of claim 14, wherein to determine the posterior resection plane comprises to:
determine a primary plane that includes the distal medial condyle and the distal lateral condyle;
determine an offset of a cortex plane relative to the primary plane based on the selected size and the one or more surgical preferences;
identify a boundary curve indicative of an intersection of the cortex plane and the femoral bone model;
locate an apex point of the boundary curve, wherein the apex point is an anterior-most point of the boundary curve;
determine an apex plane that includes the apex point and is perpendicular to an anterior-posterior direction; and
determine a posterior resection plane based on the apex plane and the one or more dimensions of the prospective femoral implant of the selected size.

16. The computing system of claim 14, wherein to select the desired femoral implant size comprises to select a femoral implant size of the plurality of possible femoral implant sizes associated with a smallest determined difference between the target value and the average of the first distance and the second distance.

17. The computing system of claim 14, wherein to determine the difference between the target value and the average of the first distance and the second distance comprises to determine the difference, d, according to $d=|\frac{1}{2}(DIST_{LAT}+DIST_{MED})-(impThk+1.5\ mm)|$,
wherein $DIST_{MED}$ is the first distance;
wherein $DIST_{LAT}$ is the second distance; and
wherein impThk is the thickness of the prospective femoral implant.

18. One or more non-transitory machine-readable storage media for femoral implant sizing in advance of a surgical procedure on a patient's knee comprising a plurality of instructions stored thereon that, in response to execution by a computing device, causes the computing device to:
preoperatively acquire at least one image of a distal femur of the patient;
generate a femoral bone model from the at least one image;
locate a distal medial condyle, a distal lateral condyle, a posterior medial condyle, and a posterior lateral condyle of the femoral bone model;
determine a primary plane that includes the distal medial condyle and the distal lateral condyle;
determine an offset of a cortex plane relative to the primary plane based on the selected size and one or more surgical preferences;
identify a boundary curve indicative of an intersection of the cortex plane and the femoral bone model;
locate an apex point of the boundary curve, wherein the apex point is an anterior point of the boundary curve;
determine an apex plane that includes the apex point and is perpendicular to an anterior-posterior direction;
determine a posterior resection plane based on the apex plane and one or more dimensions of the prospective femoral implant of the selected size;
determine a first distance between the posterior medial condyle and the posterior resection plane and a second distance between the posterior lateral condyle and the posterior resection plane;
determine a difference between a target value and an average of the first distance and the second distance, wherein the target value is associated with a thickness of the prospective femoral implant; and
select a desired femoral implant size of the plurality of possible femoral implant sizes in advance of the surgical procedure on the patient's knee, based on the determined difference between the target value and the average of the first distance and the second distance determined for each of the plurality of possible femoral implant sizes and each of the plurality of permitted flexion angles.

19. The one or more machine-readable storage media of claim 18, wherein to select the desired femoral implant size comprises to select a femoral implant size of the plurality of possible femoral implant sizes associated with a smallest determined difference between the target value and the average of the first distance and the second distance.

20. The one or more machine-readable storage media of claim 18, wherein to determine the difference between the target value and the average of the first distance and the second distance comprises to determine the difference, d, according to $d=|\frac{1}{2}(DIST_{LAT}+DIST_{MED})-(impThk+1.5\ mm)|$,
wherein $DIST_{MED}$ is the first distance;
wherein $DIST_{LAT}$ is the second distance; and
wherein impThk is the thickness of the prospective femoral implant.

* * * * *